United States Patent [19]

Allmon et al.

[11] Patent Number: 4,907,883
[45] Date of Patent: Mar. 13, 1990

[54] HIGH-TEMPERATURE LASER INDUCED SPECTROSCOPY IN NUCLEAR STEAM GENERATORS

[75] Inventors: William E. Allmon, Corapolis, Pa.; John W. Berthold, Salem, Ohio

[73] Assignee: The Babcock & Wilcox Company, New Orleans, La.

[21] Appl. No.: 195,922

[22] Filed: May 19, 1988

[51] Int. Cl.$^4$ .................... G01C 3/443; G01N 21/63
[52] U.S. Cl. .................... 356/317; 356/318; 356/323
[58] Field of Search ............... 356/317, 318, 319, 323, 356/325, 326, 328, 417; 250/458.1, 459.1, 461.1, 461.2

[56] References Cited

FOREIGN PATENT DOCUMENTS 47094 3/1982 European Pat. Off. .............. 356/73

Primary Examiner—F. L. Evans
Attorney, Agent, or Firm—Vytas R. Matas; Robert J. Edwards; Daniel S. Kalka

[57] ABSTRACT

An apparatus and method for conducting optical spectroscopy in a hostile environment comprises a light source, e.g., a laser or an incandescent light connected to a multiplexer for supplying high intensity light to at least two optical fibers. One of the optical fibers extends to a material in the hostile environment to be analyzed. The second optical fiber is connected between the multiplexer and a standard sample for yielding known spectroscopic results. Either the same or additional optical fibers are used to return light from the material to be analyzed. Each optical fiber has an end portion covered by a sheath to shield the optical fiber from the hostile environment. The sheath has an open end covered by a transparent window which is preferably made of diamond, again, to seal and protect the optical fiber in the sheath.

21 Claims, 5 Drawing Sheets

HIGH-TEMPERATURE LASER INDUCED SPECTROSCOPY IN NUCLEAR STEAM GENERATORS

FIELD AND BACKGROUND OF THE INVENTION

The present invention relates in general to optical spectroscopy, and in particular, to a new and useful apparatus and method of determining the composition of fluids and material surfaces in a high temperature environment, particularly in a nuclear steam generator.

Various forms of denting, corrosion, and mechanical damage have been observed in both once-through and recirculating nuclear steam generators. Fortunately, the magnitude of the damage has not been extensive in most units; however, some units have experienced widespread damage. Any amount of damage is very expensive to correct and undesirable. The types of damage and the number of affected units are increasing.

Damage to steam generator components, such as tubes, tube support-plates, and tubesheets are often associated with deposits on or adjacent to the damaged component. Impurities in the feedwater can concentrate on the tubes and in adjacent crevices, forming corrosive aqueous films and solid, metallic oxide deposits. Metallic oxide formation can mechanically dent the tube, whereas, aqueous films can lead to various forms of corrosion. Additionally, the aqueous film can migrate through a porous oxide deposit and corrode the tube under the deposit.

Deposits originate from impurities in the water and steam, and from corrosion of components within the steam generator. Formation of deposits may be expected when:

1. The solubility of a chemical in the water or steam is exceeded,
2. A chemical dissolves in a water droplet and is transported to a location where the water droplet evaporates, or
3. A chemical in the water or steam reacts with a steam generator component to form another chemical.

Currently, water and steam samples are cooled to ambient temperature for analysis in the laboratory or by a continuous on-line monitor. Continuous monitors offer the following advantages over laboratory analysis:

1. A continuous or semi-continuous record of the water and steam chemistry,
2. Relatively small analytical time, and
3. Unattended operation at a significantly reduced labor intensity.

However, reduction of temperature and pressure prior to the analysis is a major disadvantage of both the laboratory analysis and the continuous monitors.

Reduction of temperature and pressure can alter chemical equilibria that are established at the higher temperatures. Chemical reactions and shifts in the concentrations of the various chemical compounds can result from the current practice of sampling water and steam from the steam generators. For example, ammonium sulfate, ammonium hydrogen sulfate, and sulfuric acid may be present in the high-temperature steam; however, only the total ammonium-ion and total sulfate-ion concentrations can be measured in a condensed ambient-temperature sample.

Furthermore, the chemistry of the deposits is also difficult to ascertain from the current sampling and analysis procedures.

Water evaporates from the aqueous deposits during the shutdown procedure, thus, only the non-aqueous constituents of the deposit remain after shutdown. Deposits are frequently scraped from the surfaces after shutdown for subsequent laboratory analysis to identify those constituents. However, the amount of water that was associated with the deposit during steam generator operations cannot be determined from the laboratory analysis. Therefore, deposit concentration cannot be determined by current sampling and analysis techniques. Additionally, some water soluble deposits may be washed away during the process of steam generator shutdown.

Post-damage analysis of steam generator tubes and deposits have provided most of the available information on the damage. Some preventive measures have been recommended after careful examination of the evidence. However, a timely method is needed to detect the formation of metallic oxides and corrosive chemical solutions within the steam generators before costly damage occurs. The analysis must be done at elevated temperatures and pressures within the steam generator, since evidence can be easily altered or washed away during shutdown. Further, the ability to make these measurements at several different locations within the steam generator is necessary, since several mechanisms are responsible for damage at various locations.

Spectroscopy, using a laser as the light source, has been disclosed in U.S. Pat. No. 3,463,591 to Franken, et al; U.S. Pat. No. 3,551,053 to Windsor, et al; and U.S. Pat. No. 4,645,342 to Tanimoto, et al. In these references, the light emitted by a laser is shined on a sample to be analyzed. The sample absorbs and reflects light in a manner which is characteristic of its composition.

None of these references, however, disclose the usefulness of optical fibers for conveying light into and out of a high temperature environment to analyze the composition of materials in the high temperature environment.

An article entitled "Remote Detection of Groundwater Contaminants Using Far-Ultraviolet Laser-Induced Fluorescence", by Chudyk, et al, ANALYTICAL CHEMISTRY, Volume 57, No. 7, June 1985, discloses a UV radiation source in the form of a nitrogen-pumping dye laser, for use in conjunction with optical fibers to analyze ground water containing various pollutants. The article discloses a test conducted with groundwater in a test tube. The optical fiber was coated with Teflon (a trade name).

SUMMARY OF THE INVENTION

The present invention comprises a method and apparatus for conducting high temperature laser spectroscopy. This permits researchers to study the mechanisms of steam generator damage at various temperatures and pressures in the laboratory. The invention also allows power plant operators to observe the formation of corrosive solutions and metallic-oxide deposits on the surfaces within the steam generator during operation.

The invention may be utilized, not only to conduct optical spectroscopy at various locations in steam generators, but also to conduct this analysis in steam turbines, fossil fuel boilers and for optical spectroscopy in ground and surface water analysis.

Accordingly, an object of the present invention is to provide an apparatus for conducting optical spectroscopy in a hostile environment, comprising: a source of high intensity light; an optical fiber connected to the source of high intensity light for transmitting light therefrom, the optical fiber having an end for discharging light onto a material to be spectroscopically analyzed; a sheath defining a space around at least a part of the optical fiber carrying the end of the optical fiber, for shielding the optical fiber from the hostile environment; a window in the sheath for closing the space and for passing light transmitted through the end of the optical fiber out of the sheath; light detector means for detecting and spectroscopically analyzing light from the material which was discharged onto the material through the end of the optical fiber; and sheathed optical fiber means for transmitting light from the material to the light detector means.

A further object of the present invention is to provide a method for conducting optical spectroscopy which utilizes a source of high intensity light, optical fibers for transmitting light to and from a material to be spectroscopically analyzed, and light detector means for analyzing the light. The method includes shielding at least the end portion of the optical fiber with a sheath defining a space for containing the optical fiber and covered by a window through which light from the optical fiber is transmitted onto the material.

A still further object of the invention is to provide an apparatus for conducting optical spectroscopy in hostile environments which is simple in design, rugged in construction and economical in manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the accompanying drawings, forming a part of this specification, and in which reference numerals shown in the drawings designate like or corresponding parts throughout the same.

DESCRIPTION OF THE PREFERRED EMBODIMENTS

Figure 1:
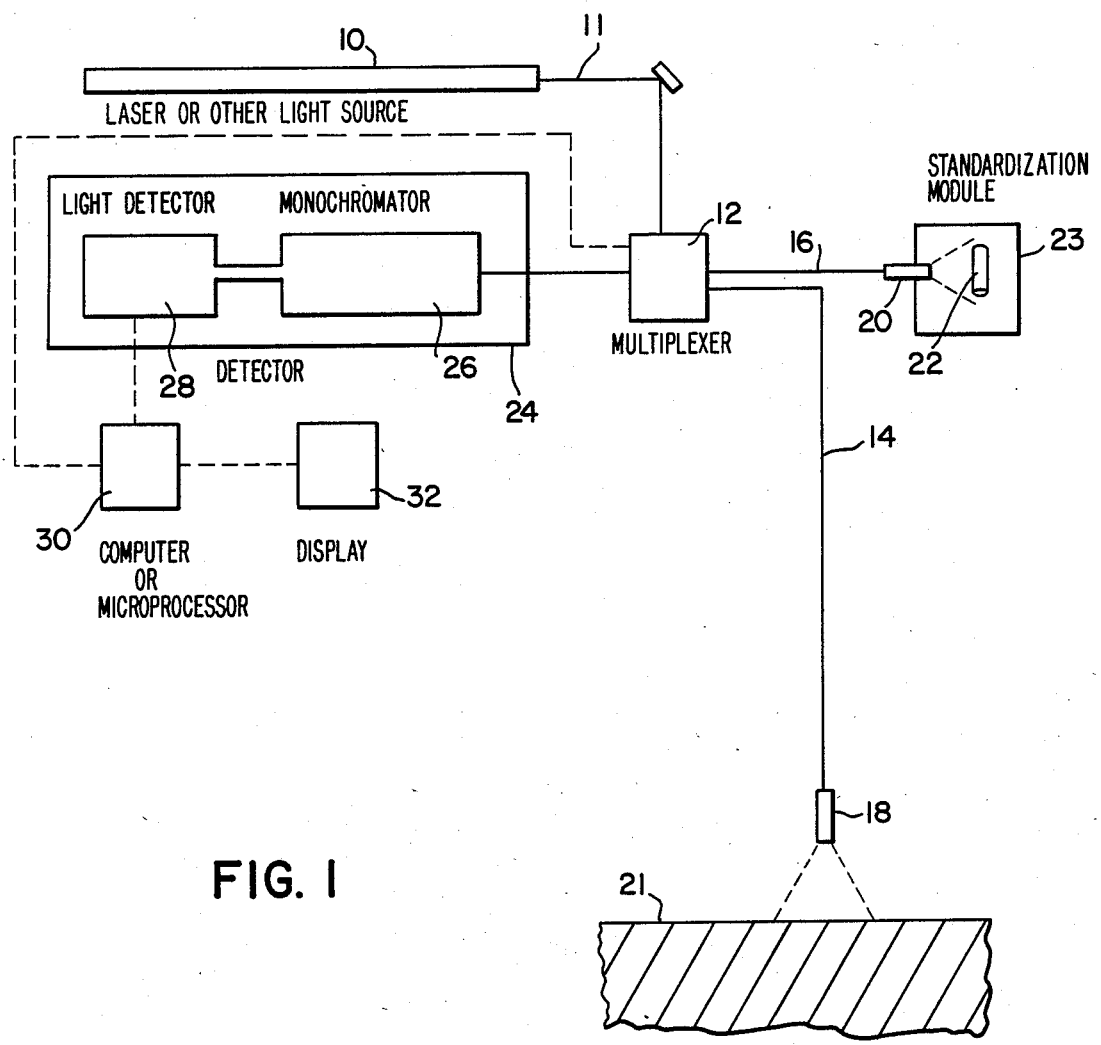
FIG. 1 is a schematic block diagram of the apparatus for conducting optical spectroscopy in accordance with one embodiment of the present invention.

Referring to the drawings in particular, the invention embodied in FIG. 1 comprises an apparatus for conducting optical spectroscopy in a hostile environment, specifically in a nuclear generator having a steam generator surface 21.

The invention comprises a source of high intensity light 10 which, in accordance with the present invention, is advantageously a pulsed, tunable dye-laser. The laser 10 is used to generate ultraviolet, visible, or infrared light in the form of a beam 11 that is conducted by known means to a multiplexer 12 which is capable of diverting the beam to a plurality of optical fibers 14 and 16.

Each optical fiber 14 and 16 is completely or partially encased by a probe assembly 18 and 20, respectively.

Light from laser 10 and multiplexer 12 is first transmitted through optical fiber 14 through probe assembly 18 onto the steam generator surface 21. In the embodiment of FIG. 1, the same optical fiber 14 acts as optical fiber means for retransmitting the light reflected from surface 21 back through multiplexer 12 to a sensitive light detector 24. Detector 24 quantifies the intensity of light that is absorbed and/or emitted after excitation by the light source 10. Detector 24 comprises a monochromator 26 which first receives the light and a light sensor 28. Signals from the light sensor 28 are spectroscopically analyzed using a computer or microprocessor 30. The results are displayed on the display 32 connected to computer or microprocessor 30.

A number of optical fiber probes 18 are used to focus light onto various surfaces within the steam generator and onto the steam itself as it travels through the generator.

Spectroscopic analysis is facilitated using a standardization module 23, which contains one of a set of sealed vials 22 each enclosing standard solutions. The spectra of these standard solutions, containing known concentrations of several chemicals, is scanned periodically to obtain calibration curves of intensity versus concentration and wavelength for each chemical of interest. The standardization module 23 is temperature controlled. The contents of the vials are illuminated using the optical fiber probe(s) 20 with light being transmitted to and from the vials by the optical fiber(s) 16.

The apparatus of FIG. 1 can be operated either automatically or manually. A concentration for each chemical on the surface or in the steam can be calculated using electrical signals from the detector 24 as wavelength is scanned using the monochromator 26. The computer is used to display, analyze and store the spectra of wavelength versus intensity for the unknown chemicals being viewed by the probe 18.

Each chemical impurity in the water, steam, aqueous film or solid deposits, absorbs and emits light at one or more distinct wavelengths. The emitted light is transmitted back to the detector 24 by the optical fiber 14 as noted above. This is possible since the wavelengths of the incident and emitted light signals are different. The optical multiplexer 12 contains lenses and hardware to mechanically switch the light path from one optical probe to the other in sequence. A plurality of optical probes similar to probe 18 can be provided at different locations in the steam generator. Switching can be performed from one probe to the other through multiplexer 12.

Monochromator 26 may be of the manual or scanning type. Light sensor 28 may be in the form of a photomultiplier tube with photon-counting electronics, a vidicon tube, a photodiode array, or a series of semiconductors. The light sensor converts the optical signals from monochromator 26 at discrete wavelengths to electric signals that can be interpreted by computer or microprocessor 30.

Figure 2:
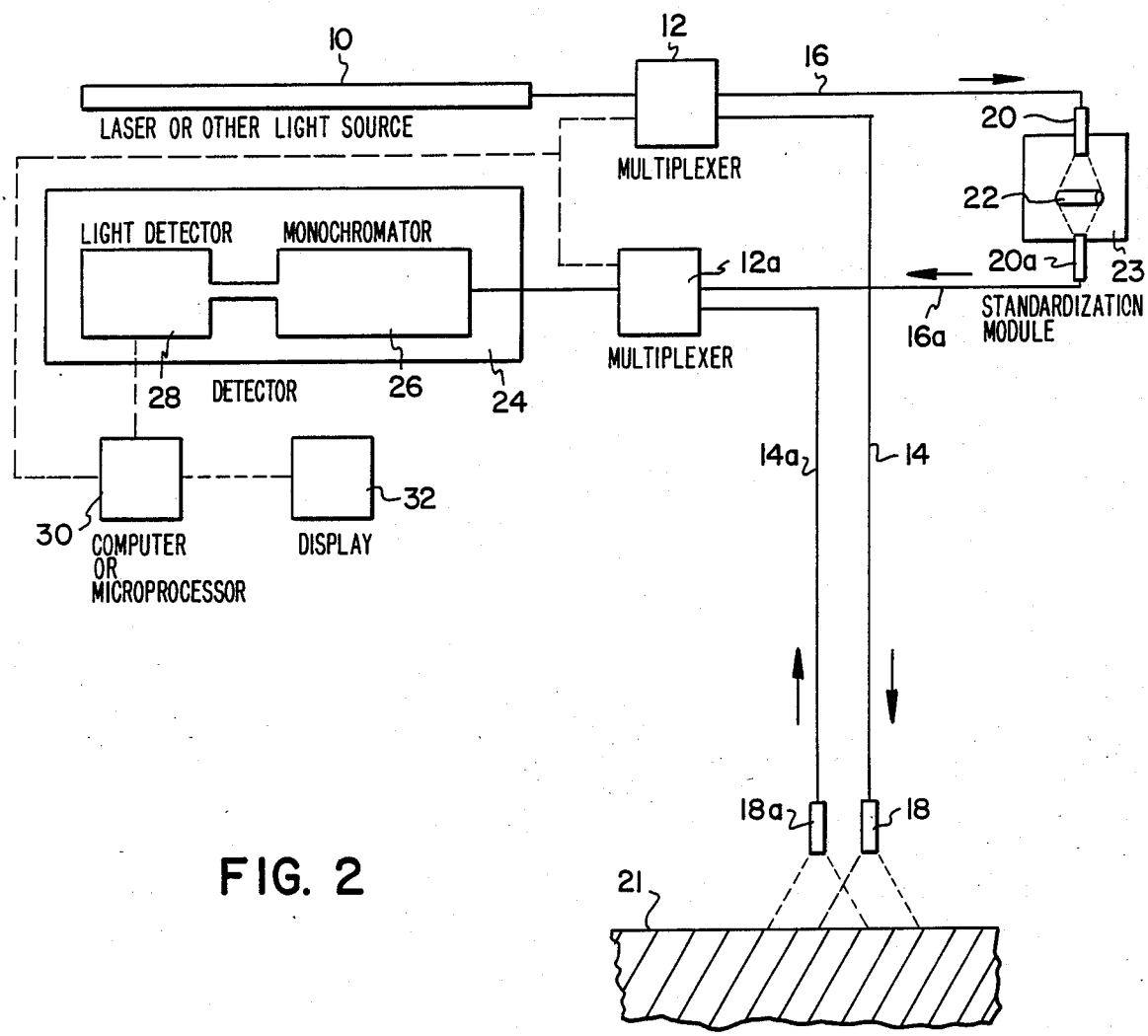
FIG. 2 is a view similar to FIG. 1 of a second embodiment of the invention.

The embodiment of FIG. 2 differs from the embodiment of FIG. 1 in that a separate probe 18a and optical fiber 14a is connected through a separate multiplexer 12a to detector 24 for returning emitted light back from surface 21 to the detector 24. A separate optical fiber 16a and probe 20a is also provided for the standardization module 23 for returning emitted light from the vial 22 through multiplexer 12a to the detector 24. The other elements of FIG. 2 operate in the same way as similarly numbered elements of FIG. 1.

The structure of probes 18, 18a, 20 and 20a can be substantially identical. Details of the structure are shown in FIG. 3.

Figure 3:
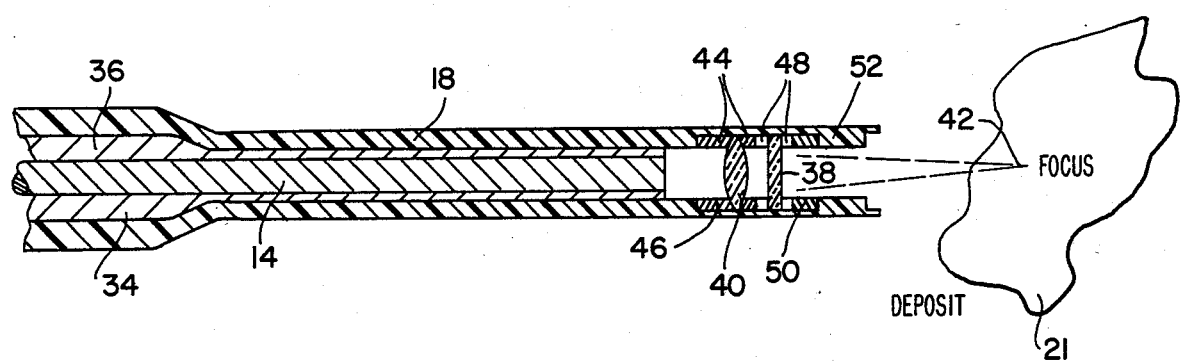
FIG. 3 is a sectional view of an optical fiber probe used in accordance with the present invention.

In FIG. 3, probe 18 comprises a sheath 34 defining an interior space 36 which contains the end portion of optical fiber 14. Space 36 is closed by a diamond window 38. If needed, a lens 40 is mounted within sheath 34 at the end of the optical fiber to focus on a spot 42 on the surface 21, or a deposit on that surface, to be analyzed.

Lens 40 is retained between seals 44 by a spacer 46. Window 38 is held between seals 48 and by a spacer 50. The stack of seals and spacers is held by a threaded retainer 52 which is threaded into the open end of sheath 34. Spacer 50 is used between retainer 52 and the outer seal 48 to avoid damage to the seal as the retainer is rotated in the sheath during assembly.

Optical fiber 14 is composed of several strands of individual fibers in order to conduct high intensity light to both eliminate fluorescence noise and damage to the fibers. A filler can be used in the space 36 between the fiber 14 and the sheath 34. The filler advantageously includes high temperature adhesive to prevent vibration damage to the fibers. Industrial diamond has been found useful as the material for window 38 to seal the interior space 36 from the outer hostile environment, including protecting the fiber and lens from attack by corrosive aqueous solution and from erosion by relatively high velocity steam. The sheath 34 is advantageously fabricated from corrosion resistant material, such as Inconel 600 (a trade name) or othe relatively inert metal.

The vial 22 in standardization module 23, both for the embodiments of FIGS. 1 and 2, may advantageously be made of Vycor (a registered trademark) glass. The module is a pressure vessel which receives pressurized inert gas to equalize the pressure between the interior and the exterior vial. The vial is filled with a solution of known chemical composition. The temperature in the module is also elevated. The module thus mimics the temperature and pressure environment for the interior of the steam generator or other hostile environment to be spectroscopically analyzed.

The present invention thus provides an in-situ apparatus and method for monitoring chemicals, solid deposits, aqueous films, steam, and water within hostile environments, such as nuclear steam generators. The method and apparatus operates on-line and at ambient conditions in the hostile environment. In this way, chemical equilibria are not altered by a reduction in temperature or pressure prior to analysis. Each chemical can be measured independently and chemical deposits and aqueous films are not washed away during shutdown before analysis takes place. Steam and water analysis is representative of local conditions near the probe. Conditions at various locations in the steam generator can also be monitored using several probes.

Many more chemicals, particularly organic chemicals, (hydrocarbons) can be measured by high temperature optical spectrometry than by current techniques. The formation of corrosive deposits and films within the generator can be observed before costly damage occurs. An early warning will allow plant operators to eliminate or pacify the deposits and solutions before costly damage occurs.

The present invention can also be utilized by researchers in laboratory studies.

The feasibility of the present invention has been confirmed by utilizing both a low-power argon laser for visible light with a wavelength of 488 nm and an incandescent source. These light sources were used to spectroscopically monitor the high temperature chemistry of vaporous hydrogen chloride, alkaline ammonium sulfate in high temperature water, acidic and neutral hydrazonium sulfate in high temperature water and steam, and sulfuric acid in high temperature water.

Pre-established concentrations of these chemicals were transferred to a transparent test chamber. The temperature was varied between 30° and 204° C. The pressure range from 0.01 to 1.77 MPa.

To verify the usefulness of diamond as the material for the window, a diamond specimen was tested in a highly hostile environment for twenty-two hours at elevated temperatures. The specimen did not exhibit any significant weight loss or loss of transparency. The twenty-two hour test was conducted at temperatures between 302° C. and 316° C. in high purity deaerated water and in acidic solutions of ammonium chloride. Initially, the concentration of ammonium chloride was controlled at several parts per million. Finally, the solution was allowed to boil and a very high concentration of acidic ammonium chloride was established adjacent to the specimen. No measurable weight loss or loss of transparency was observed.

Optical fibers were also tested over a broad temperature range from about 25° C. up to 350° C. The fibers exhibited very little variation in transparency. Changes in light transmission through a one meter section of optical fiber was less than 4% over the entire temperature range. Temperature variations of a few degrees at specific locations within the steam generator would, thus, cause very little variation in optical transmission.

Figure 4:
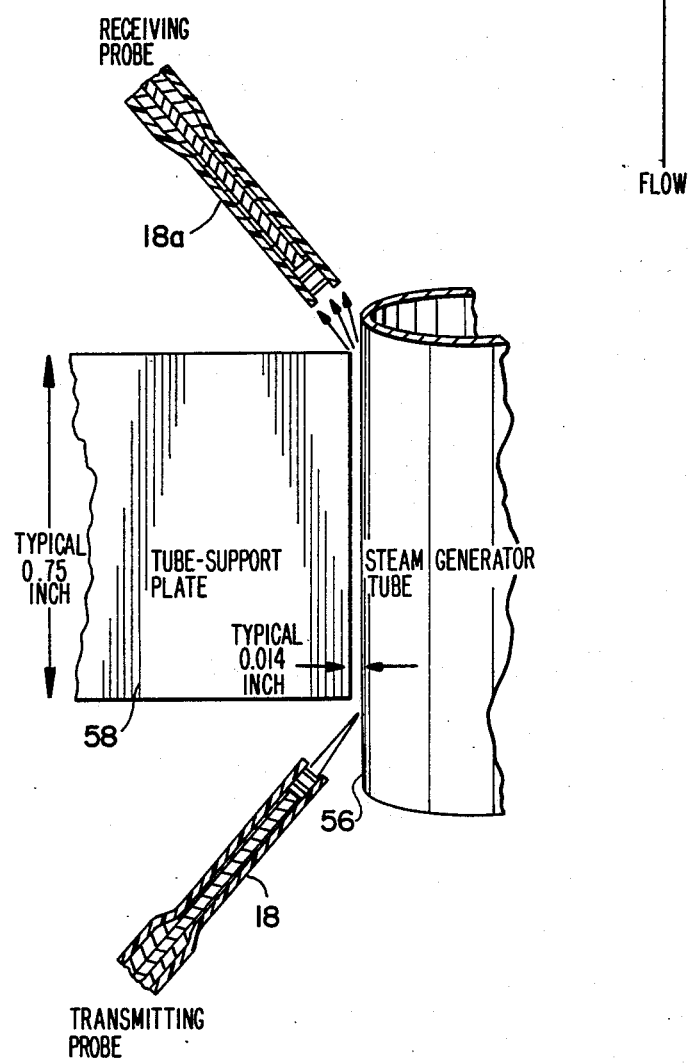
FIG. 4 is a schematic diagram of an arrangement for using transmitting and receiving probes in accordance with the present invention, for spectroscopically analyzing the outer surface of the steam generator tube near a tube support plate therefor.

FIG. 4 shows the location of a transmitting probe 18 and a receiving probe 18a in the vicinity of a crevice between a steam generator tube 56 and a tube support plate 58. In a typical steam generator, plate 58 has a thickness of approximately 0.75 inches, while the crevice between the tube and the plate is approximately 0.014 inches wide. Other dimensions can be accommodated. The direction of steam flow is indicated by the arrow.

Figure 5:
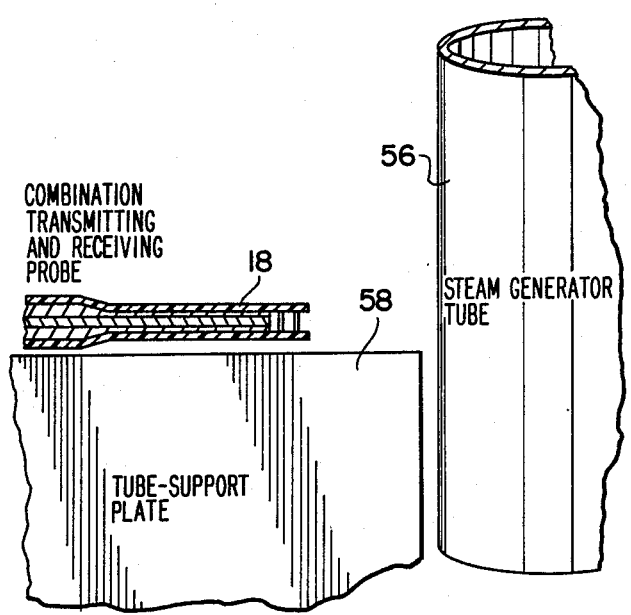
FIG. 5 is a view similar to FIG. 4 showing the use of the probe for analyzing the outer surface of a steam generator tube just outside its tube support plate.

FIG. 5 shows another use of the invention where probe 18, acting both for transmission and reception of light, is mounted on the tube support plate 58 facing the tube 56, for viewing the surface of the tube near the crevice, between tube and plate.

Figure 6:
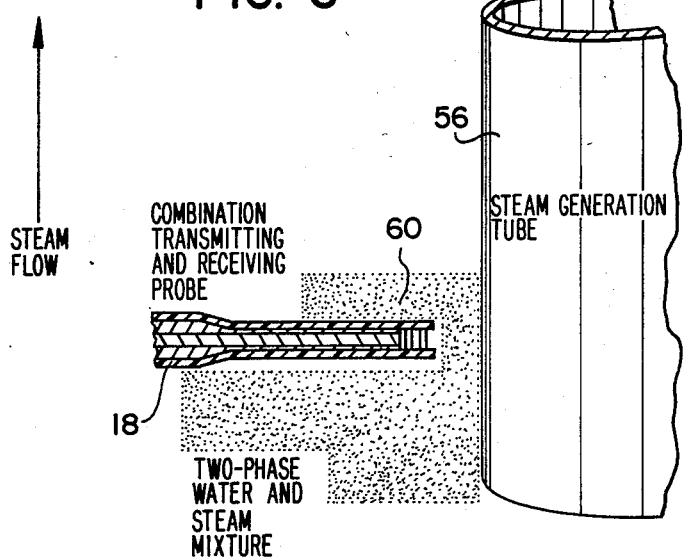
FIG. 6 is a view similar to FIG. 4 showing the use of the inventive probe for monitoring the concentration of solutions around a steam generator tube.

FIG. 6 shows the placement of probe 18 for transmission and reception in a two-phase water and steam mixture 60 surrounding a steam generator tube 56. In this case, the chemical solutions on the steam generator tube near departure from nucleate boiling are measured.

Figure 7:
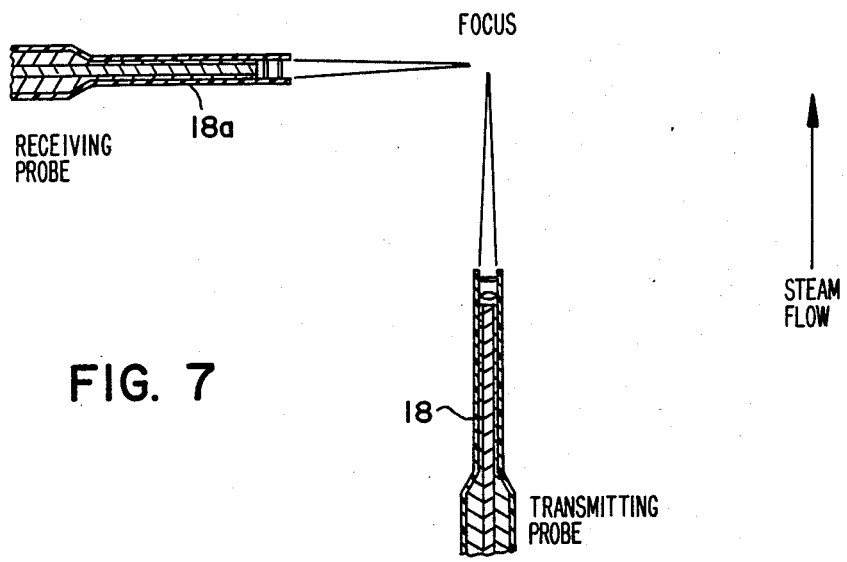
FIG. 7 is a view similar to FIG. 4 showing the use of a pair of probes in accordance with the present invention for monitoring steam phase concentration of chemicals.

FIG. 7 shows the arrangement of a transmitting probe 18 at an angle to a receiving probe 18a with focused spots overlapped to monitor steam phase concentrations of chemicals in the steam flow.

Figure 8:
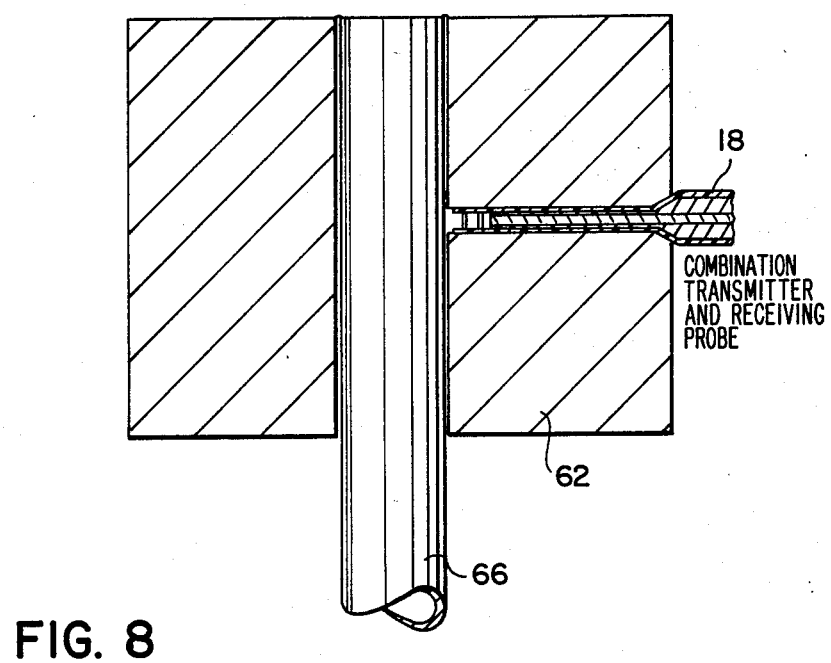
FIG. 8 is a view similar to FIG. 4 showing the use of a probe in accordance with the invention in a simulated tube sheet or tube support plate to monitor the chemistry of the crevice.

FIG. 8 shows an installation of a combination transmission and reception probe 18 in a simulated upper or lower tubesheet 62 for monitoring the chemistry in the crevice between the tubesheet 62 and a steam generator tube 66.

While specific embodiments of the invention have been shown and described in detail to illustrate the application of the principles of the invention, it will be understood that the invention may be embodied otherwise without departing from such principles.

The invention claimed is:

1. An apparatus for conducting optical spectroscopy in a hostile environment, comprising:
   a source of high intensity light;
   an optical fiber connected to the source of high intensity light for transmitting light therefrom, the optical fiber having an end for discharging light onto a material to be spectroscopically analyzed;
   a sheath defining a space around at least a part of the optical fiber carrying the end of the optical fiber for shielding the optical fiber from the hostile environment;
   a window in the sheath for closing the space and for passing light transmitted through the end of the optical fiber out of the sheath;
   light detector means for detecting and spectroscopically analyzing emitted light from the material;
   an optical fiber means for transmitting the emitted light from the material to the light detector means;
   a standardization module for containing a sample having a known composition and being exposed to known temperature and pressure conditions;
   an additional optical fiber connected to said module for transmitting light to the sample in said module;
   multiplexer means connected to said first-mentioned and additional optical fibers for switching sequentially between said optical fibers, said source of high intensity light being connected to said multiplexer means for supplying light for said optical fibers to said multiplexer means and said detector means being connected to said multiplexer means for receiving light from said multiplexer means; and
   additional optical fiber means for returning light from said module to said detector through said multiplexer means.

2. An apparatus according to claim 1, wherein said source of high intensity light comprises a laser.

3. An apparatus according to claim 1, wherein said source of high intensity light comprises an incandescent light.

4. An apparatus according to claim 1, wherein said light detector means comprises a monochromator for receiving light from said optical fiber means and a light detector for sensing light from said monochromator.

5. An apparatus according to claim 1, wherein said window is made of diamond.

6. An apparatus according to claim 1, wherein said first-mentioned optical fiber means comprises said first-mentioned optical fiber for both transmitting and receiving light, said additional optical fiber means comprising said additional optical fiber for transmitting and receiving light.

7. An apparatus according to claim 1, wherein said multiplexer means includes a first multiplexer connected to said source of high intensity light and to said first-mentioned and additional optical fibers, said multiplexer means including a second multiplexer, said optical fiber means comprising a second optical fiber connected to said second multiplexer and extending to the material to be spectroscopically analyzed for returning light from the material, said additional optical fiber means comprising a third optical fiber connected between said module and said second multiplexer for returning light from said module to said second multiplexer, said second multiplexer being connected to said light detector means.

8. An apparatus according to claim 1, including a filler between said optical fiber and said sheath for supporting said optical fiber in said sheath.

9. An apparatus according to claim 8, including at least one lens in said sheath between said end of said optical fiber and said window for focusing light being discharged from said end of said optical fiber.

10. An apparatus according to claim 9, including a seal engaged between said lens and said sheath, a seal engaged between said window and said sheath, a spacer between said seals of said lens and said window, a retainer fixed to an open end of said sheath and an additional spacer between said retainer and said window seal for retaining said seals and said spacers in said sheath.

11. An apparatus according to claim 10, wherein said window is made of diamond.

12. An apparatus according to claim 11, wherein said source of high intensity light comprises a laser.

13. An apparatus according to claim 11, wherein said source of high intensity light comprises an incandescent light.

14. A method for conducting optical spectroscopy in a hostile environment, comprising:
   generating a high intensity light;
   conducting the high intensity light through an optical fiber to a material contained in the hostile environment;
   shielding at least a portion of the optical fiber near the material in a sheath, an end of the optical fiber near the material facing an open end of the sheath;
   closing the open end of the sheath with a transparent window that is resistant to the hostile environment;
   transmitting light from the material to light detector means for spectroscopically analyzing the light from the material; and
   transmitting the high intensity light to a sample having known composition and under known conditions;
   transmitting light from the sample back to the detector means for spectroscopically analyzing light from the sample; and
   using the analysis of the light from the sample as a standard for analyzing light from the material.

15. A method according to claim 14, including the window being made of diamond.

16. A method according to claim 15, including transmitting light to the sample through an additional optical fiber, returning light from the material through the first-mentioned optical fiber and returning light from the sample through the additional optical fiber.

17. A method according to claim 15, including returning light from the material through a second optical fiber and returning light from the sample through a third optical fiber.

18. A method according to claim 16, including connecting the first-mentioned and additional optical fibers to a multiplexer, the light source comprising a laser, connecting the laser to the multiplexer for sequentially applying light to the optical fibers, and connecting the detector means to the multiplexer for sequentially receiving light from the optical fibers.

19. A method according to claim 17, including generating the high intensity light, using a laser, connecting a laser to a first multiplexer, connecting the multiplexer to the optical fiber for transmitting light to the material, connecting an additional optical fiber between the multiplexer and the sample for transmitting light to the sample, connecting a second multiplexer to the detector means, connecting a second optical fiber between the material and the second multiplexer for returning light from the material.

20. A method according to claim 17, including generating the high intensity light, using an incandescent light, connecting an incandescent light to a first multiplexer, connecting the multiplexer to the optical fiber for transmitting light to the material, connecting an additional optical fiber between the multiplexer and the sample for transmitting light to the sample, connecting a second multiplexer to the detector means, connecting a second optical fiber between the material and the second multiplexer for returning light from the material.

21. A method according to claim 14, including focusing light from the optical fiber through the window using the lens in the sheath.

* * * * *